US011523615B2

(12) United States Patent
Hagen

(10) Patent No.: US 11,523,615 B2
(45) Date of Patent: *Dec. 13, 2022

(54) MICROBIAL INOCULANT COMPOSITIONS AND METHODS

(71) Applicants: RAISON, LLC, Sioux Falls, SD (US); Tony Hagen, Sioux Falls, SD (US)

(72) Inventor: Tony Hagen, Sioux Falls, SD (US)

(73) Assignee: RAISON, LLC, Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/635,152

(22) PCT Filed: Aug. 3, 2018

(86) PCT No.: PCT/US2018/045234
§ 371 (c)(1),
(2) Date: Jan. 29, 2020

(87) PCT Pub. No.: WO2019/028398
PCT Pub. Date: Feb. 7, 2019

(65) Prior Publication Data
US 2021/0084906 A1    Mar. 25, 2021

Related U.S. Application Data

(60) Provisional application No. 62/541,422, filed on Aug. 4, 2017, provisional application No. 62/660,830, filed on Apr. 20, 2018, provisional application No. 62/663,069, filed on Apr. 26, 2018, provisional application No. 62/672,198, filed on May 16, 2018.

(51) Int. Cl.
| *A01N 63/27* | (2020.01) |
| *A01N 63/32* | (2020.01) |
| *A01N 63/20* | (2020.01) |
| *A01N 63/22* | (2020.01) |
| *C12N 1/20* | (2006.01) |

(52) U.S. Cl.
CPC ............. *A01N 63/27* (2020.01); *A01N 63/20* (2020.01); *A01N 63/22* (2020.01); *A01N 63/32* (2020.01); *C12N 1/20* (2013.01)

(58) Field of Classification Search
CPC ........ A01N 63/27; A01N 63/32; A01N 63/20; A01N 63/22; C12N 1/20
See application file for complete search history.

(56) References Cited

U.S. PATENT DOCUMENTS

| 2013/0255338 A1* | 10/2013 | Lopez-Cervantes | C12N 1/14 71/7 |
| 2013/0337518 A1 | 12/2013 | Razavi-Shirazi et al. | |
| 2016/0376627 A1 | 12/2016 | Zengler et al. | |
| 2021/0084895 A1 | 3/2021 | Hagen | |

FOREIGN PATENT DOCUMENTS

| AR | P180102210 | 8/2018 |
| AR | P180102211 | 3/2020 |
| AU | 2018309093 | 3/2020 |
| AU | 2018309149 | 3/2020 |
| BR | 112020002388-4 | 8/2018 |
| BR | 112020002401-5 | 8/2018 |
| CA | 3072583 | 1/2020 |
| CA | 3071953 | 2/2020 |
| EP | 2018840925 | 3/2020 |
| EP | 2018841406 | 3/2020 |
| HK | 62020021870.4 | 12/2020 |
| HK | 62020021877.9 | 12/2020 |
| MX | MX/a/2020/001413 | 2/2020 |
| MX | MX/a/2020/001414 | 2/2020 |
| WO | WO 2012/150610 A2 | 8/2012 |
| WO | WO 2017/131821 A1 | 8/2017 |
| WO | PCT/US2018/045215 | 8/2018 |
| WO | PCT/US2018/045234 | 8/2018 |

OTHER PUBLICATIONS

Sharma et al., "Phosphate solubilizing microbes: sustainable approach for managing phosphorus deficiency in agricultural soils", SpringerPlus vol. 2, Article No. 587 (2013) (Year: 2013).*
U.S. Appl. No. 16/635,149, filed Year: 2020.*
Lugtenberg, et al. "Plant Growth Promotion by Microbes", 2013, Molecular Microbial Ecology of the Rhizosphere, vol. 2, First Edition: pp. 561-574.
Sharma, et al., "Phosphate solubilizing microbes: sustainable approach for managing phosphorus deficiency in agricultural soils", SpringerPlus, vol. 2, Article No. 587 (2013).
Sivaskthi, et al., "Biocontrol potentially of plant growth promoting bacteria (PGPR)—*Pseudomonas fluorescens* and *Bacillus subtilis*: a review", Apr. 2014, African Journal of Agricultural Research, vol. 9, No. 16, pp. 1265-1277.
Wu, X, et al., "Comparative genomics and functional analysis of niche-specific adaptation in Pseudomonas putida", FEMS Microbiology Reviews, Mar. 2011, vol. 35, No. 2, pp. 299-323.
International Search Report and Written Opinion were dated Nov. 29, 2018 by the International Searching Authority for International Application No. PCT/US2018/045234, filed on Aug. 3, 2018 and published as WO/2019/028398 dated Feb. 7, 2019 (Applicant—Raison, LLC) (5 Pages).
International Preliminary Report on Patentability was dated Feb. 4, 2020 by the International Searching Authority for International Application No. PCT/US2018/045234, filed on Aug. 3, 2018 and published as WO/2019/028398 dated Feb. 7, 2019 (Applicant—Raison, LLC) (6 Pages).
International Search Report and Written Opinion were dated Nov. 26, 2018 by the International Searching Authority for International Application No. PCT/US2018/045215, filed on Aug. 3, 2018 and published as WO/2019/028385 dated Feb. 7, 2019 (Applicant—Raison, LLC) (4 Pages).
International Preliminary Report on Patentability was dated Feb. 4, 2020 by the International Searching Authority for International Application No. PCT/US2018/045215, filed on Aug. 3, 2018 and published as WO/2019/028385 dated Feb. 7, 2019 (Applicant—Raison, LLC) (6 Pages).

(Continued)

*Primary Examiner* — Ruth A Davis
(74) *Attorney, Agent, or Firm* — Ballard Spahr LLP

(57) ABSTRACT

A microbial inoculant composition includes aquatic bacterial species. In some embodiments, the microbial inoculant composition includes at least one of an aquatic *Pseudomonas* spp. and a *Clostridium* spp.

14 Claims, 7 Drawing Sheets

(56) References Cited

OTHER PUBLICATIONS

U.S. Appl. No. 62/672,198, filed May 16, 2018, Tony Hagen.
U.S. Appl. No. 62/672,190, filed May 16, 2018, Tony Hagen.
U.S. Appl. No. 62/663,069, filed Apr. 26, 2018, Tony Hagen.
U.S. Appl. No. 62/663,067, filed Apr. 26, 2018, Tony Hagen.
U.S. Appl. No. 62/660,830, filed Apr. 20, 2018, Tony Hagen.
U.S. Appl. No. 62/660,836, filed Apr. 20, 2018, Tony Hagen.
U.S. Appl. No. 62/541,422, filed Aug. 4, 2017, Tony Hagen.
U.S. Appl. No. 16/635,149, filed Jan. 29, 2020, Tony Hagen.
Mowlick, et al. "Proliferation of diversified clostridial species during biological soil disinfestation incorporated with plant biomass under various conditions", 2013, Appl Microbiol Biotechnol, vol. 97:8365-8379.
Yang, et al., "Growth-promoting *Sphingomonas paucimobilis* ZJSH1 associated with *Dendrobium officinale* through phytohormone production and nitrogen fixation", Microbial Biotechnology, vol. 7, No. 6, pp. 611-620, 2014.

\* cited by examiner

MICROBIAL INOCULANT COMPOSITIONS AND METHODS

CROSS-REFERENCE TO RELATED APPLICATION

This application is a national stage application under 35 U.S.C. § 371 of International Application No. PCT/US2018/045234, filed on Aug. 3, 2018, which claims the benefit of priority to U.S. Provisional Patent Application No. 62/541,422, filed Aug. 4, 2017; U.S. Provisional Patent Application No. 62/660,830, filed Apr. 20, 2018; U.S. Provisional Patent Application No. 62/663,069, filed Apr. 26, 2018; and U.S. Provisional Patent Application No. 62/672,198, filed May 16, 2018. The content of these earlier filed applications are hereby incorporated by reference.

SUMMARY

This disclosure describes, in one aspect, a microbial inoculant composition. Generally, the microbial inoculant composition includes an aquatic *Pseudomonas* spp. and a *Clostridium* spp., wherein the aquatic *Pseudomonas* spp. causes a plant to produce a plant hormone.

In some embodiments, the aquatic *Pseudomonas* spp. is *P. moraviensis* or *P. fluorescens*.

In some embodiments, the *Clostridium* spp. is *Clostridium saccharobutylicum*.

In some embodiments, the microbial inoculant composition further includes a *Bacillus* spp. In some of these embodiments, the *Bacillus* spp. is *B. megaterium*, *B. subtilis*, or *B. licheniformis*.

In some embodiments, the microbial inoculant composition further includes an aquatic *Delftia* spp.

In some embodiments, the microbial inoculant composition further includes an aquatic *Chryseobacterium* spp.

In some embodiments, the microbial inoculant composition further includes *Brevundimonas kwangchunensis*, *Fictibacillus barbaricus/Bacillus barbaricus*, a *Prosthecobacter* spp., *Sphingobacterium multivorum*, or a *Sphingomonas* spp.

In some embodiments, the microbial inoculant composition further includes *Bacillus megaterium*, *Bacillus amyloliquifaciens*, *Bacillus subtilus*, *Bacillus pumilus*, *Sphingosinicella microcystinivorans*, *Pseudomonas chlororaphis*, *Pseudomonas mandelii*, *Pseudomonas umsongensis*, a *Clostridium* spp., *Arthrobacter ramosus*, *Streptomyces yogyakartensis*, an *Arthrobacter* spp., a *Xanthomonas* spp., or *Chryseobacterium indologenes*.

In another aspect, this disclosure describes a plant that includes adhered to a least a portion of the plant.

In another aspect, this disclosure describes a seed having any embodiment of the microbial inoculant composition summarized above adhered to at least a portion of the seed. In another aspect, this disclosure describes a method that includes applying any embodiment of the microbial inoculant composition summarized above to a tissue of a plant.

In another aspect, this disclosure describes a method that includes applying any embodiment of the microbial inoculant composition summarized above to a surface of a seed.

In another aspect, this disclosure describes a method that includes applying any embodiment of the microbial inoculant composition summarized above to a seed bed.

In another aspect, this disclosure describes a method that includes applying any embodiment of the microbial inoculant composition summarized above to a field comprising a plurality of plants.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
FIG. 1. Effect of microbial inoculant composition on soybeans. Soybeans in the middle and right are treated with an exemplary microbial composition. Soybeans on the left are untreated. Treated soybeans have bigger leaves and more branching.
Figure 2:
FIG. 2. Effect of microbial inoculant composition on soybeans. Soybeans on the left are treated with an exemplary microbial composition. Soybeans on the right are untreated. Treated soybeans show reduced leaf wilt and greater leaf size.
Figure 3:
FIG. 3. Effect of microbial inoculant composition on wheat. Wheat on the right is untreated. Wheat in the middle is treated at the foliar stage with an exemplary microbial inoculant composition. Wheat on the left is treated with the same microbial inoculant composition at the seed coat stage. Untreated wheat averaged 29 heads, foliar-treated wheat averaged 40 heads, seed-coat-treated wheat averaged 61 heads.
Figure 4:
FIG. 4. Effect of microbial inoculant composition on canola. Canola on the right was untreated. Canola on the left was treated with an exemplary microbial inoculant composition. Treated canola shows increased branching and increased pod number.
Figure 5:
FIG. 5. Effect of microbial inoculant composition on corn. Upper cob is from an untreated plant. Lower cob is from a plant treated with an exemplary microbial inoculant composition. The lower cob shows an increase in kernels per ring compared to the untreated cob. Difference in size of the kernels is due to the treated corn being at an earlier stage of development than the untreated corn.

This disclosure describes microbial inoculant compositions that include aquatic microbial species for application to terrestrial plants. In some embodiments, the inoculant mixture also includes a species that produces and/or maintains a microenvironment in the plant that is suitable for other microbes in the inoculant mixture to thrive.

A loss of biodiversity within a soil matrix can lead to yield depression of agricultural crops. Microbial inoculants can increase solubilization, uptake, and/or assimilation of nutrients such as, for example, carbon, nitrogen, potassium. phosphorus, selenium, cobalt, zinc, and copper. Microbial inoculants also can reduce plant pathogen damage to crops by stimulating plant production of a stable and continuous source of plant hormones that enhance growth. While microorganisms capable of promoting plant growth and plant production can occur naturally in soil, the mere presence of the microbes does not guarantee the successful integration of the microbes.

In at least one embodiment, as described below, the microbial inoculant composition can function endophytically within at least one plant to maintain an available electron state that is available for use within the plant's metabolic process. That is, the microbial inoculant composition can act as an ionic catalyst to either accept or remove an electron to make the electron available to or remove the electron from the plant. This process can occur, in the absence of such a microbial inoculant composition, when a plant switches from photosynthesis during the day to respiration at night and vice versa. The microbial inoculant composition, when applied to the plant, supports the plant by making nutrients chemically available so the plant can produce hormones at a sufficient level to promote growth.

The microbial inoculant composition can inoculate the plant by being in close proximity and/or direct physical contact with the plant. As an example, a droplet of water including the microbial inoculant composition can be deposited on the plant, and thereby not deposited in the soil and not absorbed by the roots.

This disclosure describes novel microbial inoculant compositions isolated from an aquatic environment for application to terrestrial plants. In some embodiments, the inoculant mixture also includes a species that produces and/or maintains a microenvironment in the plant that is suitable for other microbes in the inoculant mixture to thrive.

Generally, the microbial inoculant composition includes a *Pseudomonas* spp. and a *Clostridium* spp., such as, for example, *P. fluorescens* and *C. saccharobutylicum*.

In some embodiments, the microbial inoculant composition further includes one or more of *Agrobacterium tumefaciens* (TPD7005), *Bacillus megaterium* (TPD7007), *Bacillus megaterium* (TPD 7008), *Agrobacterium rhizogenes* (TPD7009), *Microbacterium testaceum* (TPD7010), *Bacillus megaterium* (TPD7011), *Microbacterium* spp. (TPD 7012), *Pedobacter kribbensis* (TPD70013), *Janthinobacterium lividum* (TPD7014), *Bacillus racemilacticus* (TPD7015), *Bacillus megaterium* (TPD 7018), *Delftia* spp. (TPD3002), *Chryseobacterium* spp. (TPD3003), *Bacillus licheniformis, Brevundimonas kwangchunensis* (TPD3004), *Fictibacillus barbaricus/Bacillus barbaricus* (TPD3005), *Prosthecobacter* spp. (TPD3006), *Lactobacillus plantarum* (TPD3007), *Sphingobacterium multivorum, Sphingomonas* spp. (TPD3009), *Sphingosinicella microcystinivorans* (TPD3010), *Pseudomonas chlororaphis, Pseudomonas mandelii, Pseudomonas umsongensis, Clostridium saccharobutylicum* (TPD3014), *Arthrobacter ramosus* (TPD3015), *Streptomyces yogyakartensis* (TPD3016), *Arthrobacter* spp. (TPD3017), *Xanthomonas* spp., *Chryseobacterium indologenes* (TPD3019), or *Lactobacillus plantarum*.

Table 1 shows 16S RNA analysis and/or whole genome shotgun sequencing project data for exemplary members of the microbial inoculant composition.

TABLE 1

| Species | Designation | GenBank Accession No. |
| --- | --- | --- |
| *Pseudomonas veronii* | TPD3012 | MH190219.1 |
| *Pseudomonas mandelii* | TPD3013 | MH221124.1 |
| *Pseudomonas moraviensis* | TPD3001 | MH190053.1 |
| *Pseudomonas protegens* | TPD3011 | MH221127.1 |
| *Pantoea agglomerans* | TPD7001 | MH190052.1 |
| *Clostridium saccharobutylicum* | TPD3014 | MH189851.1 |
| *Clostridium saccharobutylicum* | TPD7003 | MH192394.1 |

TABLE 1-continued

| Species | Designation | GenBank Accession No. |
| --- | --- | --- |
| *Erwinia aphidicola* | TPD7004 | MH190220.1 |
| *Serratia liquefaciens* | TPD7002 | MH190215.1 |
| *Pedobacter kribbensis* | TPD70013 | MH221086.1 |
| *Janthinobacterium lividum* | TPD7014 | MH221099.1 |
| *Bacillus racemilacticus* | TPD7015 | MH221098.1 |
| *Sphingomonas* spp. | TPD3009 | QDFK00000000.1 |
| *Agrobacterium tumefaciens* | TPD7005 | QDFL00000000.1 |
| *Bacillus megaterium* | TPD7018 | QDFM00000000.1 |
| *Sphingomonas* spp. | TPD3009 | QDFN00000000.1 |
| *Bacillus megaterium* | TPD7007 | QDFO00000000.1 |
| *Bacillus megaterium* | TPD7008 | QDFP00000000.1 |
| *Arthrobacter* spp. | TPD3018 | QDFQ00000000.1 |
| *Agrobacterium rhizogenes* | TPD7009 | QDFR00000000.1 |
| *Sphingomonas melonis* | TPD3008 | QDFS00000000.1 |
| *Microbacterium testaceum* | TPD7010 | QDFT00000000.1 |
| *Bacillus megaterium* | TPD7011 | QDFU00000000.1 |
| *Microbacterium* spp. | TPD7012 | QDFV00000000.1 |

Finally, in some embodiments, the microbial inoculant composition further includes one or more of yeast strain TAH3020 or yeast strain TAH3021.

The microbial inoculant composition can promote plant growth (e.g., increase leaf size, increase root mass), decrease the impact of stress, decrease water consumption, increase solubility and/or assimilation of nutrients, increase feed value, increase decay of carbon-containing molecules so that the organic molecules are more readily available to the plant, increase production of hormones in plants, and/or increase plant metabolism (thereby decreasing the time to fruit). Moreover, in legumes, the microbial inoculant composition can increase pod numbers, increase root growth, increase nodulation, and/or increase the number of branches per plant. In some embodiments, the microbial inoculant composition can be applied to contact and/or interact endophytically with the plant.

In particular, bacteria in the microbial inoculant composition can produce 1-aminocyclopropane-1-carboxylate (ACC) deaminase. ACC can lower plant ethylene levels, often a result of various stresses such as, for example, stress to heat and/or drought. ACC can interact synergistically with the plant and bacterial auxin, indole-3-acetic acid (IAA). ACC-producing bacteria not only can directly promote plant growth, but also can protect against flooding, drought, salt, flower wilting, metals, organic contaminants, bacterial pathogens, and fungal pathogens.

In particular, decreasing water consumption can increase solubilization of minerals and/or fertilizers so that water requirements are reduced to transport the minerals and/or fertilizers from the roots, increase root development so that soil nutrients can be obtained from a greater area and/or water can be obtained from deeper in the soil, and/or reduce daily heat stress. Reducing daily heat stress allows the plant to better acquire $CO_2$, thereby metabolize more sugars and increase yield, regulate pH, and/or produce more energy during daylight hours.

The microbial inoculant compositions can include additional microbial species or other additives to induce the plant to perform desired physiological, metabolic, or other activity.

For example, in certain embodiments, the microbial inoculant compositions can include one or more of the following microbial species: an *Acetobacteraceae*, spp. (e.g., *Acidisphaera* spp.), an *Acetivibrio* spp. (e.g., *Acetivibrio cellulolyticus*), an *Acidiphilium* spp., an *Acidimicrobiaceae* spp. (e.g., an *Acidimicrobium* spp., an *Aciditerrimonas* spp.), an *Acidobacteriales* spp. (e.g., an

*Acidobacteriaceae* spp. [e.g., an *Acidobacterium* spp.]), an *Acidothermus* spp., an *Acidovorax* spp. (e.g., *Acidovorax citrulli*), an *Acinetobacter* spp. (e.g., *Acinetobacter lwoffii*), an *Actinoallomurus* spp. (e.g., *Actinoallomurus iriomotensis*), an *Actinocatenispora* spp. (e.g., *Actinocatenispora rupis*), an *Actinomadura* spp., an *Actinomycetales* spp. (e.g., an *Actinomyces* spp.), an *Actinoplanes* spp. (e.g., *Actinoplanes auranticolor*), an *Actinopolymorpha* spp. (e.g., *Actinopolymorpha pittospori*), an *Actinotalea* spp. (e.g., *Actinotalea fermentans*), an *Adhaeribacter* spp. (e.g., *Adhaeribacter terreus*), an *Aeromicrobium* spp. (e.g., *Aeromicrobium fastidiosum*), an *Afipia* spp., an *Agromyces* spp. (e.g., *Agromyces ulmi, Agromyces subbeticus*), an *Alcaligenaceae* spp., an *Algoriphagus* spp., an *Alkaliflexus* spp., an *Alphaproteobacteria* spp., an *Alsobacter* spp. (e.g., *Alsobacter metallidurans*), an *Altererythrobacter* spp., an *Alteromonadaceae* spp., an *Amaricoccus* spp., an *Aminobacter* spp., an *Amycolatopsis* spp. (e.g., *Amycolatopsis iriomotensis, Amycolatopsis vancoresmycina*), an *Anaeromyxobacteraceae* spp. (e.g., an *Anaeromyxobacter* spp. [e.g., *Anaeromyxobacter dehalogenans*]), an *Ancylobacter* spp., an *Angustibacter* spp. (e.g., *Angustibacter peucedani*), an *Aquabacterium* spp., an *Aquicella* spp., an *Armatimonadetes* spp., an *Arenimonas* spp. (e.g., *Arenimonas oryziterrae*), an *Arsenicicoccus* spp. (e.g., *Arsenicicoccus dermatophilus*), an *Arthrobacter* spp. (e.g., *Arthrobacter pascens, Arthrobacter tumbae*), an *Asanoa* spp. (e.g., *Asanoa ishikariensis*), an *Azohydromonas* spp. (e.g., *Azohydromonas australica*), an *Azonexus* spp., an *Azospira* spp. (e.g., *Azospira oryzae*), an *Azospirillum* spp. (e.g., *Azospirillum lipoferum*), an *Azotobacter* spp. (e.g., *Azotobacter chroococcum*), a *Bacillaceae* spp. (e.g., a *Bacillus* spp. [e.g., *Bacillus acidiceler, Bacillus aphidicola, Bacillus senegalensis, Bacillus megaterium, Bacillus subtilis*]), a *Bacteroidetes* spp. (e.g., a *Bacteroidales* spp. [e.g., a *Bacteroides* spp.]), a *Bauldia* spp. (e.g., *Bauldia* consociate), a *Bdellovibrionaceae* spp., a *Beijerinckia* spp., a *Blastococcus* spp. (e.g., *Blastococcus saxobsidens*), a *Blastomonas* spp., a *Bordetella* spp. (e.g., *Bordetella hinzii*), a *Bosea* spp., a *Bradyrhizobiaceae*, spp. (e.g., *Bradyrhizobium* spp. [e.g., *Bradyrhizobium elkanii, Bradyrhizobium yuanmingense*]), a *Brevibacteriaceae* spp., a *Brevundimonas* spp. (e.g., *Brevundimonas lenta*), a *Bryobacter* spp., a *Burkholderiales* spp. (e.g., a *Burkholderiaceae* spp. [e.g., a *Burkholderia* spp.]), a *Brucellaceae* spp., a *Buttiauxella* spp. (e.g., *Buttiauxella izardii*), a *Byssovorax*, spp., a *Caldilineales* spp. (e.g., a *Caldilineaceae* spp., a *Caldilinea* spp.]), a *Caloramator* spp., a *Candidatus* spp. (e.g., *Candidatus brocadiaceae, Candidatus entotheonella, Candidatus koribacter, Candidatus nitrosoarchaeum, Candidatus phytoplasma, Candidatus saccharibacteria, Candidatus solibacter*), a *Carnobacterium* spp., a *Catenuloplanes* spp., a *Catellatospora* spp., (e.g., *Catellatospora citrea*), a *Caulobacteraceae* spp. (e.g., a *Caulobacter* spp. [e.g., *Caulobacter tundrae*]), a *Cellulosimicrobium* spp. (e.g., *Cellulosimicrobium cellulans*), a *Cellvibrio* spp. (e.g., *Cellvibrio* vulgaris), a *Cellulomonas* spp. (e.g., *Cellulomonas terrae*), a *Chelatococcus* spp. (e.g., *Chelatococcus asaccharovorans*, a *Chitinophagaceae* spp., a *Chromobacteriaceae* spp., a *Chloroflexales* spp. (e.g., a *Chloroflexaceae* spp. [e.g., a *Chloroflexus* spp.]), a *Chthoniobacter* spp. (e.g., *Chthoniobacter flavus*), a *Chryseobacterium* spp., a *Citrobacter* spp., a *Clavibacter* spp. (e.g., *Clavibacter michiganensis*), a *Clostridiaceae* spp. (e.g., a *Clostridium* spp. [e.g., *Clostridium bowmanii, Clostridium gasigenes, Clostridium uliginosum, Clostridium vincentii*]), a *Comamonadaceae* spp. (e.g., a *Comamonas,* spp. [e.g., *Comamonas koreensis*]), a *Conexibacteraceae* spp. (e.g., a *Conexibacter* spp. [e.g., *Conexibacter woesei*]), a *Coxiellaceae* spp., a *Crenotrichaceae* spp. a *Cryomorphaceae* spp., a *Cryobacterium* spp. (e.g., *Cryobacterium mesophilum*), a *Cupriavidus* spp. (e.g., *Cupriavidus campinensis*), a *Curtobacterium* spp., a *Cyanobacteria* spp., a *Cyclobacteriaceae* spp., a *Cystobacteraceae* spp. (e.g., a *Cystobacter* spp.), a *Cytophagaceae* spp. (e.g., a *Cytophaga* spp.), a *Defluviicoccus* spp., a *Dehalococcoidales* spp. (e.g., a *Dehalogenimonas* spp., a *Dehalococcoides* spp.), a *Denitratisoma* spp., a *Derxia* spp., a *Desulfovibrionales* spp. (e.g., a *Desulfobacteraceae* spp. [e.g., a *Desulfocapsa* spp., a *Desulfatiglans* spp., a *Desulfoforegula* spp.]), a *Desulfoglaeba* spp., a *Desulfosporosinus* spp. (e.g., *Desulfosporosinus meridiei*), a *Desulfotomaculum* spp., a *Desulfuromonadales* spp. (e.g., a *Desulfuromonas* spp.), a *Devosia* spp. (e.g., *Devosia insulae*), a *Dickeya* spp. (e.g., *Dickeya zeae*), a *Dyadobacter* spp., an *Ectothiorhodospiraceae* spp., an *Elusimicrobia* spp. (e.g., an *Elusimicrobiaceae* spp. [e.g., an *Elusimicrobium* spp.]), an *Endomicrobia* spp., an *Enhygromyxa* spp. (e.g., *Enhygromyxa salina*), an *Epilithonimonas* spp., an *Erwinia* spp. (e.g., *Erwinia persicina*), an *Exiguobacterium* spp. (e.g., *Exiguobacterium undae*), a *Ferrimicrobium* spp., a *Fictibacillus* spp., a *Flavobacteriales* spp. (e.g., a *Flavobacteriaceae*, [e.g., a *Flavobacterium* spp. such as, for example, *Flavobacterium arsenatis, Flavobacterium columnare, Flavobacterium hauense, Flavobacterium johnsoniae, Flavobacterium terrigena*]), a *Flavisolibacter* spp., a *Flexibacter* spp., a *Flindersiella* spp., a *Fodinicola* spp., a *Frankia* spp., *Frigoribacterium* spp., a *Gaiellales* spp. (e.g., a *Gaiella* spp. [e.g., *Gaiella occulta*]), a *Gallionellaceae* spp. (e.g., a *Gallionella* spp.), a *Gemmatimonadales* spp. (e.g., a *Gemmatimonadaceae* spp. [a *Gemmatimonas* spp.]), a *Gemmata* spp., a *Geoalkalibacter* spp., a *Geobacillus* spp., a *Geobacteraceae* spp. (e.g., a *Geobacter* spp.), a *Gillisia* spp., a *Glycomyces* spp. (e.g., *Glycomyces harbinensis*), a *Halomonas* spp. (e.g., *Halomonas muralis*), a *Haliangium* spp., a *Herbaspirillum* spp. (e.g., *Herbaspirillum huttiense*), a *Holophagales* spp. (e.g., a *Holophagaceae*, spp. [e.g., a *Holophaga* spp.]), a *Humibacillus* spp. (e.g., *Humibacillus xanthopallidus*), a *Hydrogenophaga* spp. (e.g., *Hydrogenophaga palleronii*), a *Hydrogenophilaceae* spp., a *Hyphomicrobiaceae* spp. (e.g., a *Hyphomicrobium* spp. [e.g., *Hyphomicrobium methylovorum*]), a *Hyphomonas* spp., an *Iamiaceae* spp. (e.g., an *Iamia* spp.), an *Ideonella* spp., an *Ignavibacteriales* spp. (e.g., an *Ignavibacteriaceae* spp. such as, for example, an *Ignavibacterium* spp.), an *Ilumatobacter* spp., an *Intrasporangiaceae* spp. (e.g., an *Intrasporangium* spp. [e.g., *Intrasporangium oryzae*]), a *Jiangella* spp., a *Kaistia* spp., a *Kaistobacter* spp., a *Kallotenuales* spp., a *Kineococcus* spp., a *Kineosporia* spp. (e.g., *Kineosporia mikuniensis*), a *Knoellia* spp., a *Kofleriaceae* spp. (e.g., a *Kofleria* spp.), a *Kribbella* spp. (e.g., *Kribbella karoonensis, Kribbella swartbergensis*), a *Labedella* spp., a *Labilitrichaceae* spp. (e.g., a *Labilithrix* spp. [e.g., *Labilithrix luteola*]), a *Lactobacillus* spp., a *Lactococcus* spp. (e.g., *Lactococcus garvieae*), a *Lapillicoccus* spp. (e.g., *Lapillicoccus jejuensis*), a *Legionellaceae* spp., a *Leifsonia* spp., a *Lentzea* spp. (e.g., *Lentzea albida*), a *Leptospira* spp., a *Leptothrix* spp., a *Leucobacter* spp. (e.g., *Leucobacter tardus*), a *Longilinea* spp., a *Lysinibacillus* spp. (e.g., *Lysinibacillus sphaericus*), a *Lysobacter* spp., a *Marinimicrobium* spp., a *Marinobacter* spp., a *Marmoricola* spp., a *Massilia* spp. (e.g., *Massilia timonae*), a *Melioribacteraceae* spp. (e.g., a *Melioribacter* spp.), a *Mesorhizobium* spp. (e.g., *Mesorhizobium loti, Mesorhizobium plurifarium*), a *Methylibium* spp., a *Methylobacillus* spp. (e.g., *Methylobacillus flagellates*), a *Methylobacteriaceae* spp. (e.g., a *Methylo-* bacterium spp. [e.g., *Methylobacterium adhaesivum*]), a *Methylocella* spp., a *Methylococcaceae* spp. (e.g., a *Methylobacter* spp.), a *Methylocystaceae* spp. (e.g., a *Methylocystis* spp. [e.g., *Methylocystis echinoides*]), a *Methylosinus* spp., a *Methyloversatilis* spp., a *Microbacteriaceae* spp. (e.g., a *Microbacterium* spp. [e.g., *Microbacterium kitamiense*], a *Microcella* spp. [e.g., *Microcella alkaliphile*]), a *Micrococcaceae* spp., a *Microlunatus* spp., a *Microvirga* spp. (e.g., *Microvirga aerilata, Microvirga subterranean*), a *Mycobacteriaceae* spp. (e.g., a *Mycobacterium* spp. [e.g., *Mycobacterium sacrum, Mycobacterium salmoniphilum, Mycobacterium septicum*]), a *Micromonosporaceae* spp. (e.g., a *Micromonospora* spp. [e.g., *Micromonospora rhodorangea*]), a *Modestobacter* spp. (e.g., *Modestobacter multiseptatus*), a *Moorella* spp., a *Myxococcales* spp., a *Nakamurella* spp., a *Nannocystaceae* spp. (e.g., a *Nannocystis* spp. [e.g., *Nannocystis exedens*]), a *Neorhizobium* spp. (e.g., *Neorhizobium huautlense*), a *Niastella* spp., a *Nitriliruptor* spp., a *Nitrosomonadaceae* spp. (e.g., a *Nitrosomonas* spp. [e.g., *Nitrosomonas communis, Nitrosomonas ureae*]), a *Nitrosopumilales* spp. (e.g., a *Nitrosopumilaceae* spp.), a *Nitrosospira* spp., a *Nitrosovibrio* spp. (e.g., *Nitrosovibrio tenuis*), a *Nitrospirales* spp. (e.g., a *Nitrospira* spp.), a *Nocardiaceae* spp. (e.g., a *Nocardia* spp. [e.g., *Nocardia anaemiae*]), a *Nocardioidaceae* spp. (e.g., a *Nocardioides* spp. [e.g., *Nocardioides albus, Nocardioides iriomotensis, Nocardioides islandensis, Nocardioides maritimus, Nocardioides perillae, Nocardia pneumoniae*]), a *Nocardiopsis* spp. (e.g., *Nocardiopsis synnemataformans*), a *Nonomuraea* spp. (e.g., *Nonomuraea kuesteri*), a *Nordella* spp., a *Novosphingobium* spp., an *Ochrobactrum* spp. (e.g., *Ochrobactrum haematophilum*), an *Ohtaekwangia* spp., an *Olivibacter* spp. (e.g., *Olivibacter soli*), an *Opitutaceae* spp., an *Oryzihumus* spp., an *Oxalobacteraceae* spp., an *Oxalophagus* spp. (e.g., *Oxalophagus oxalicus*), a *Paenibacillus* spp., (e.g., *Paenibacillus graminis, Paenibacillus chondroitinus, Paenibacillus validus*), a *Pantoea* spp. (e.g., *Pantoea agglomerans*), a *Paracoccus* spp., a *Paracraurococcus* spp., a *Parastreptomyces* spp., a *Pasteuriaceae* spp., (e.g., a *Pasteuria* spp.), a *Pedosphaera* spp. (e.g., *Pedosphaera parvula*), a *Pedobacter* spp. (e.g., *Pedobacter tournemirensis, Pedobacter kribbensis, Pedobacter kwangyangensis*), a *Pelagibacterium* spp. (e.g., *Pelagibacterium halotolerans*), a *Pelobacteraceae* spp. (e.g., a *Pelobacter* spp.), a *Peptoclostridium* spp. (e.g., *Peptoclostridium clostridium sordellii*), a *Peredibacter* spp., a *Phaselicystidaceae* spp., a *Phenylobacterium* spp., a *Phycicoccus* spp., a *Phycisphaerae* spp., a *Phyllobacterium* spp. (e.g., *Phyllobacterium trifolii*), a *Pigmentiphaga* spp., a *Planococcus* spp., a *Planomicrobium* spp., (e.g., *Planomicrobium novatatis*), a *Planctomycetes* spp. (e.g., a *Pirellula* spp., such as *Pirella staleyi*), a *Plesiocystis* spp., a *Polaromonas* spp., a *Polyangiaceae* spp., a *Procabacteriacae* spp., a *Prolixibacter* spp., a *Promicromonospora* spp., (e.g., *Promicromonospora sukumoe*), a *Prosthecobacter* spp., a *Prosthecomicrobium* spp., a *Pseudoalteromonas* spp., a *Pseudoclavibacter* spp., (*Pseudoclavibacter helvolus*), a *Pseudolabrys* spp., (e.g., *Pseudolabrys taiwanensis*), a *Pseudomonadaceae* spp. (e.g., *Pseudomonas fluorescens, Pseudomonas flavescens, Pseudomonas protegens, Pseudomonas veronii, Pseudomonas rhodesiae, Pseudomonas koreensis, Pseudomonas moorei, Pseudomonas baetica*), a *Pseudonocardia* spp., (e.g., *Pseudonocardia zijingensis, Pseudonocardia carboxydivorans*), a *Pseudorhodoferax* spp., a *Pseudoxanthobacter* spp., a *Ralstonia* spp., a *Pseudoxanthomonas* spp., a *Ramlibacter* spp., a *Reyranella* spp. (e.g., *Reyranella massiliensis*), a *Rheinheimera* spp., a *Rhizobiales* spp. (e.g., a *Rhizobiaceae* spp., a *Rhodobiaceae* spp.), a *Rhizobium* spp. (e.g., *Rhizobium etli*), a *Rhizomicrobium* spp., a *Rhodobacterales* spp. (e.g., a *Rhodobacter* spp.), a *Rhodococcus* spp. (e.g., *Rhodococcus gordoniae, Rhodococcus kroppenstedtii, Rhodococcus wratislaviensis*), a *Rhodocyclales* spp. (e.g., a *Rhodocyclaceae* spp.), a *Rhodomicrobium* spp., a *Rhodoplanes* spp. (e.g., *Rhodoplanes elegans*), a *Rhodopseudomonas* spp., a *Rhodospirillales* spp. (e.g., a *Rhodospirillaceae* spp.), a *Rhodothermus* spp., a *Rickettsiaceae* spp.), a *Roseateles* spp., a *Roseomonas* spp., a *Rubrivivax* spp. (e.g., *Rubrivivax gelatinosus*), a *Rubrobacterales* spp. (e.g., a *Rubrobacter* spp.), a *Ruminococcaceae* spp., a *Saccharopolyspora* spp. (e.g., *Saccharopolyspora gloriosa*), a *Sandaracinus* spp., a *Saprospiraceae* spp., a *Serratia* spp. (e.g., *Serratia proteamaculans*), a *Shimazuella* spp. (e.g., *Shimazuella kribbensis*), a *Shinella* spp. (e.g., *Shinella granuli*), a *Sideroxydans* spp. (e.g., *Sideroxydans lithotrophicus, Sideroxydans paludicola*), a *Sinobacteraceae* spp. (e.g., a *Steroidobacter* spp.), a *Sinorhizobium* spp., a *Solibacteraceae* spp. (e.g., a *Solibacter* spp.), a *Solirubrobacteraceae* spp. (e.g., a *Solirubrobacter* spp.), a *Sorangium* spp. (e.g., *Sorangium cellulosum*), a *Sphaerobacterales* spp. (e.g., a *Sphaerobacteraceae* spp. such as, for example, a *Sphaerobacter* spp.), a *Sphingobacteriales* spp. (e.g., a *Sphingobacteriaceae* spp. such as, for example, a *Sphingobacterium* spp.), a *Sphingobium* spp. (e.g., *Sphingobium herbicidovorans*), a *Sphingomonadaceae* spp. (e.g., a *Sphingobium* spp. [e.g., *S. xenophagum*], a *Sphingomonas* spp. [e.g., *S. wittichii*]), a *Sphingopyxis* spp. (e.g., *Sphingopyxis macrogoltabida*), a *Sphingosinicella* spp., a *Spirochaetales* spp. (e.g., a *Spirochaeta* spp.), a *Sporichthyaceae* spp. (e.g., a *Sporichthya* spp.), a *Stackebrandtia* spp. (e.g., *Stackebrandtia nassauensis*, a *Stella* spp., a *Stenotrophomonas* spp. (e.g., *Stenotrophomonas maltophilia*), a *Stigmatella* spp. (e.g., *Stigmatella erecta*), a *Streptacidiphilus* spp., a *Streptoalloteichus* spp., a *Streptomycetaceae* spp. (e.g., a *Streptomyces* spp. [e.g., *Streptomyces aculeolatus, Streptomyces clavuligerus, Streptomyces fradiae, Streptomyces ghanaensis, Streptomyces glauciniger, Streptomyces hebeiensis, Streptomyces heteromorphus, Streptomyces mashuensis, Streptomyces microflavus, Streptomyces netropsis, Streptomyces phaeochromogenes, Streptomyces roseogriseolus, Streptomyces variabilis, Streptomyces vayuensis, Streptomyces viridodiastaticus, Streptomyces viridochromogenes, Streptomyces xylophagus, Streptomyces xinghaiensis*]), a *Sulfuricella* spp., a *Syntrophobacterales* spp. (e.g., a *Syntrophorhabdaceae* spp. such as, for example, a *Syntrophobacter* spp. [e.g., *S. wolinii*], a *Syntrophorhabdus* spp., a *Syntrophaceae* spp., a *Syntrophus* spp.), a *Taibaiella* spp., a *Tepidamorphus* spp., a *Terrabacter* spp., a *Terriglobus* spp., a *Terrimonas* spp., a *Tetrasphaera* spp. (e.g., *Tetrasphaera* elongate), a *Thermoanaerobacterales* spp. (e.g., a *Thermoanaerobacteraceae* spp.), a *Thermoflavimicrobium* spp., a *Thermoleophilaceae* spp., a *Thermomonosporaceae* spp., a *Thioalkalivibrio* spp., a *Thiobacillus* spp., (e.g., *Thiobacillus denitrificans*), a *Thiobacter* spp., a *Thiomonas* spp., a *Thiorhodovibrio* spp., a *Tolumonas* spp., (e.g., *Tolumonas auensis*), a *Variovorax* spp., (e.g., *Variovorax paradoxus*), a *Verrucomicrobiales* spp., (e.g., a *Verrucomicrobia* subdivision 3 spp.), a *Vibrionales* spp., a *Woodsholea* spp., (e.g., *Woodsholea maritima*), a *Xanthomonadaceae* spp., (e.g., a *Xanthomonas* spp.), a *Zoogloea* spp., or a *Zooshikella* spp.

In at least one embodiment, the following can act as an antagonist to at least one of the microbial species listed above, e.g., *Pseudomonas fluorescens, Pseudomonas mandelii: Streptornyces hygroscopicus, Mycobacterium*

*vaccae, Agrobacterium turnefaciens, Bacillus megaterium, Bacillus amyloliquifaciens, Bacillus subtilus, Bacillus pumilus,* a *Shingomonas* spp., *Sphingomonas melonis,* an *Arthrobacter* spp., *Agrobacterium rhizogenes, Serratia proteatnaculans, Microbacterium testaceum,* a *Pseudomonas* spp., an *Erwinia* spp., *Pantoea agglomerans, Pseudomonas raandelii,* a *Microbacterium* spp., *Clostridium saccharobutylicum, Pseudomonas moraviensis, Pantoea vagans, Serratia liquefaciens, Pedobacter kribbensis, Tolumonas auensis, Janthinobacterium lividum, Bacillus racemilacticus, Sporolactobacillus laevolacticus, Brevundimonas mediterranea, Pantoea cloacae, Clostridium acidisoli, Erwinia aphidicola, Bacillus arbutinivorans, Paenibacillus graminis, Pseudornonas veronii, Pseudomonas rhodesiae, Pseudornonas koreensis, Tolumonas auensis, Pseudomonas moorei, Pseudomonas baetica,* and/or *Pseudomonas protegens.*

In certain embodiments, a microbial species that provides insecticidal activity can be added to the microbial inoculant. Suitable microbes can include bacteria or fungi that produce phytochemicals that have insecticidal or insect repelling properties. In some of these embodiments, the microbial species can be a bacterium such as, for example, *B. thuringiensis, B. pipilhae, Photohabdus luminescens, Pseudomonas entomohpilia, Envinia aphidicola,* etc., or a fungus such as, for example, *Beaveria bassiana, Lagenidium giganteum,* etc.

The microbial inoculant composition also can include one or more non-microbial additives. For example, the microbial inoculant composition can include one or more macro nutrients or one or more micro nutrients such as, for example, carbon, nitrogen, potassium. phosphorus, zinc, magnesium, selenium, chromium, tin, manganese, cobalt, zinc, and/or copper. Suitable macro nutrients or micro nutrients may enhance the longevity of the bacteria and microbes leading to a longer shelf life. Also, adding a slow growth supporting carbon source (e.g., glycerol, a vegetable oil, lignin, etc.) may be beneficial. This can also function as a stratification media for more anaerobic and aerobic microbes in a single package.

As another example, the microbial inoculant composition can include one or more plant hormone such as, for example, an auxin. Exemplary suitable plant hormones include auxins such as indole-3-acetic acid (IAA), 4-chloroindole-3-acetic acid (4-CI-IAA), 2-phenylacetic acid (PAA), indole-3-butyric acid (IBA), indole-3-propionic acid (IPA), naphthaleneacetic acid (NAA). Adding a plant hormone to the inoculant composition can provide an initial boost of plant growth and/or establish a faster growth pattern in a field that has, for example, sustained crop damage and is replanted so that the replanted crops need to mature faster than usual.

As another example, the microbial inoculant composition can include a fertilizing agent. A fertilizing agent may include an organic fertilizing agent or an inorganic fertilizing agent. Exemplary inorganic fertilizing agents may include, for example, nitrogen, phosphorus, potassium, zinc, and/or magnesium. Exemplary organic fertilizers may include, for example, compost, manure, agricultural waste, bone meal, humic extract of peat, and the like or other as known by persons skilled in the art.

As yet another example, the microbial inoculant composition can include one or more adhesive agents to promote the composition adhering to a plant once it is applied to a plant or crop field. One exemplary adhesive agent can include any biocompatible adhesive agent that can be mixed with the microbial inoculant composition and dried onto a seed. As used herein, "biocompatible" refers to an agent that is compatible with the other components of the composition, and not deleterious to the seed or plant to which a formulation that includes the biocompatible component is applied. Suitable adhesive agents include talc, graphite, gum agar, cane sugar, dextrin, commercial potato shellac, starch, or other as known by persons skilled in the art.

In another aspect, this disclosure describes a plant to which any embodiment of the microbial inoculant composition described above is applied. Suitable plants include terrestrial plants, such as, for example, crop plants, trees (deciduous or coniferous), feed plants (e.g., alfalfa), biomass crops, or horticultural plants.

Exemplary crop plants can include wheat, oats, barley, cotton, sugar beets, flax, peanuts, beans, soybeans, potatoes, tomatoes, peppers, corn (especially following sugar beet syndrome), cucumbers, lettuce, cabbage, cauliflower, broccoli, radishes, carrots, celery, jalapeno peppers, okra, Brussels sprouts, watermelon, musk melon, apples, pears, grapes, peaches, oranges, grapefruit, plums, apricots, lemons, avocados, bananas, cassava, sweet potato, pineapple, dates, figs, almonds, walnuts, hazel nuts, pecans, cashews, tobacco, *cannabis*, oregano, cilantro, sage, saffron, cinnamon, agave, other herbs, or other as known by persons skilled in the art.

Exemplary biomass crop plants can include, poplar trees, switch grass, duck weed, elephant grass, moringa, or other as known by persons skilled in the art.

Exemplary trees to which any embodiment of the microbial inoculant composition can be applied include, for example, cottonwood, willow, birch, poplar, or other as known by persons skilled in the art.

Exemplary horticultural plants can include roses, vines, tubered perennials, petunias, hollyhocks, daffodils, reed sedge, tulips, chrysanthemums, or other as known by persons skilled in the art.

For example, when applied to wheat, the microbial inoculant composition can result in increased stem count, increased tillering, increased head weights, increased seed count, increased size of leaves, increased kernel count, increased kernel weight, increased protein content in the kernel, increased height of the stem, and/or increased overall surface area of the flag leaf. In one example, untreated wheat yielded approximately 50 bushels per acre. A comparable field was treated with a microbial inoculant composition at the foliar stage, yield was increased to 75 bushels per acre. A comparable field treated at the seed coat stage yielded more than 100 bushels per acre. The wheat treated at the seed coat stage had a 30% increase in the number of kernels, a 20% increase in kernel weight, and a 2% increase in the ratio of protein in the kernel. (FIG. 3).

The effect of the microbial inoculant composition can be mitigated to some extent if used in combination with certain fungicides such as, for example, propiconazole. If the fungicide is applied at the manufacturer recommended rate, the efficacy of the microbial inoculant composition can be reduced. For example, when applied to wheat before jointing, the fungicide kills bacteria in the microbial inoculant composition and the effects of the microbial inoculant composition can be negated. If the fungicide is applied to wheat after jointing, one can still see an increase in head count, but increases in leaf size, kernel size, protein ratio, etc. are mitigated.

When applied to soybeans, the microbial inoculant composition can result in, for example, increased branching, increased pod count, increased leaf count, increased leaf size, increased number of root nodules, and/or increased size of root nodules (FIG. 1, FIG. 2). In at least one embodiment, the microbial inoculant composition can be applied at an end of a vegetative state of the soybeans. Results of applying the microbial inoculant composition to soybeans can include an increase of anywhere from 4 to 8 bushels per acre. In at least one example result, one field had an increase of 16 bushels per acre. In at least one example method, the microbial inoculant composition is applied to the seed coat, an herbicide is added to damage the leaves of the plant, a Hydra effect occurs, additional herbicide is added to the leaves, and the stalks are broken to further induce the Hydra effect.

When applied to potatoes, the microbial inoculant composition can result in, for example, increased early stage rooting, increased rhizome production, increase the weight of salable potatoes by promoting the first and second set over the third and fourth set, produce darker coloration, increase the above-ground mass of the plant, and/or increase the total weight of tubers produced per acre. In at least one example, the microbial inoculant composition can be applied to potatoes and/or rooted plants, such as sugar beets, onions, carrots, etc. In at least one example of application to onions, a single onion can grow to approximately 3.25 lbs. In contrast, an onion that has not received the microbial inoculant composition can grow to about 0.25 to 0.5 lbs. In addition, in at least one example, onions with the application can have increased volume with less time to get to the onion's normal size, mentioned above. In at least one example, application of the microbial inoculant composition on sugar beets, without splitting, can result in a weight increase of 300%. In at least one example, application of the microbial inoculant composition on sweet potatoes can result in a two-fold increase in size of the sweet potato.

When applied to trees, the microbial inoculant composition can result in, for example, increased height, increased number of leaves in the first year, and/or increased total mass of the tree.

When applied to tomatoes, the microbial inoculant composition can result in, for example, increased flowering, increased bud count, better regeneration after browsing, and/or increased number of tomatoes produced per plant.

When applied to alfalfa, the microbial inoculant composition can result in, for example, increased volume of plant material per acre and/or reduced effects of stress flowering. Reducing the effects of stress flowering allows one to wait longer to cut the alfalfa before it turns woody. In spring, this can allow a farmer to allow the alfalfa to grow longer before it turns woody, thereby allowing the farmer to spend time planting other crops that would otherwise be necessary to cut the alfalfa before it turns woody. Waiting longer between cuttings before the alfalfa turns woody allows one to obtain more tonnage without sacrificing the quality and/or nutritional value of the alfalfa. Also, applying the microbial inoculant composition to alfalfa can result a decrease in the lignin content of the plant as a percentage of total plant biomass. The decreased lignin content can increase the food value of the plant. Applying the microbial inoculant composition also can increase leaf size and/or increase root mass of the plant. Increasing leaf size, like decreasing the lignin content, can increase the food value of the plant. To support the increased photosynthetic surface area that results from the increased leaf size, pants treated with the microbial inoculant composition can exhibit increased root mass, thereby increasing the carbon in the soil. When applied to alfalfa, it may be desirable to reapply the microbial inoculant composition after each cutting.

In at least one embodiment, in response to applying the microbial inoculant composition, alfalfa production can increase by 15 percent in alfalfa production by tonnage. In at least one embodiment, a *Rhizobium* species and/or minerals including cobalt can be added along with or be added within the microbial inoculant composition. In at least one example, inoculation of alfalfa occurred two weeks prior to cutting, resulting in a 35% increase in tonnage.

The effects of the microbial inoculant composition on alfalfa can be reduced somewhat when there is a zinc deficiency and/or molybdenum deficiency in the soil and/or alfalfa, such as may occur when alfalfa is repeatedly grown in the same field. The mineral deficiency can become a growth-limiting factor. The mineral deficiency can affect the activity of indole-3-acetic acid (IAA) and other growth hormones, affecting the ability of the plant to convert nitrate to ammonium.

When applied to sunflowers, the microbial inoculant composition can result in, for example, increased surface area of flower heads, increased sugars in the flowers, and/or a Hydra effect. In at least one embodiment, a greater than or equal to increase in surface area of flower heads was observed. Increased sugars in the flowers can increase attraction of pollinators and, therefore, increase pollination. The microbial inoculant composition can be added to the sunflower plants in response to the flower heads being at least 3 inches tall, just post-emergence. In at least one example, a Hydra effect including cutting off a first head and growing two replacement heads that are full heads 10½ inches tall was observed. In this example, this can double the yield of sunflower heads.

When applied to bell peppers, the microbial inoculant composition can result in, for example, increased weight of the fruit, increased stem rigidity, and/or increased stem strength.

When applied to corn, the microbial inoculant composition can result in, for example, increased number of kernels per ring and/or increased phosphorus solubility for the plant, thereby mitigating effects of sugar beet syndrome in which an untreated corn plant can manifest stunted plant growth, decreased yield, and/or the corn having a purple appearance. In at least one embodiment, in response to the microbial inoculant composition being applied to corn, a yield increase of one ton to 2.5 tons per acre of dry land silage can result. The application of the microbial inoculant composition is not time dependent; the microbial inoculant composition can be applied at any time from V1 to tassel. When applied to grain corn, in at least one embodiment, within a week of the tassels a 4.8 to 6.8 bushel per acre yield increase can result. In at least one example where corn following sugar beet (CFS) syndrome has occurred, application of the microbial inoculant composition at seed coat or at post-emergence can stabilize phosphorus, leading to the corn overcoming the CFS syndrome effects. CFS syndrome can refer to when corn planting directly follows the planting of sugar beets, which can lead to stunting, shortened internodes, purpling, and/or reduction in vigor.

When applied to small grains, such as wheat barley, oats, rye, etc., applying the microbial inoculant composition prior to a flag leaf can increase the size of the flag leaf, which can, in turn, increase the supply of carbohydrates available to feed the grains. That is, the mass of the small grain can be increased, which can increase tonnage of the small grains. In at least one example, early application prior to a tiller (e.g., stem) and flag leaf can increase a quantity of stems and increase the weight of the small grain, increasing the tonnage by from 50% to as much as 100%. Also, when applied to the seed coat of small grains, the microbial inoculant composition can increase head count. In at least one example, the microbial inoculant composition can be applied rye or winter wheat in the fall season and again in the spring season.

When applied to cabbage, the microbial inoculant composition can include at least one or more of *B. thuringiensis* and *B. amyloliquifaciens*. In at least one example, in response to harvesting cabbage plants that received application of the microbial inoculant composition, the cabbage plants produced multiple heads per plant. In contrast, cabbage plants that did not receive application of the microbial inoculant composition died post-harvest.

When applied to grass, such as prairie grass, lawn grass, sod, etc., the microbial inoculant composition can be applied to both the seed and the grass, increasing leaf size and promoting a darker color, increased growth, and increased root growth that can capture more carbon and/or store increased amounts of carbon in the soil.

When applied to hemp, the microbial inoculant composition can result in, for example, increased height, increased width, increase root size, increased stem girth, increased number of buds, increased size of buds, increased number of seed structures, and/or increased size of seed structures.

When applied to duckweed, the microbial inoculant composition can result in increased root growth. In at least one example, where duckweed can grow up to approximately one (1) inch, application of the microbial inoculant composition can result in growth up to 12 inches. Further, the increased growth of the duckweed can result in increased phosphotransacetylase (pta) biomass as feed. In at least one example, in response to stressing the duckweed plant (such as with dehydration, heat, pH change, etc.) as it is harvested, a breakdown of leucine can occur. The breakdown of leucine can change the amino acid composition and provide a product with lower or no levels of leucine.

When applied to horticultural plants, the microbial inoculant composition can result in, for example, increased growth (whether measured by height, length, or total mass), increased number of blossoms, deeper coloration, faster growing vine, increased size of vine leaves, increased numbers of runners, increased length of runners, and/or tuber perennials carrying over bacteria from the inoculant to subsequent years. In at least one embodiment, application of the microbial inoculant composition to horticultural plants can maintain turgor pressure longer than plants that where the microbial inoculant composition was not applied, causing the plant to maintain aesthetic appeal longer, which can result in greater retail sales and fewer discarded plants.

In at least one embodiment, post-stress damage can occur to any of the above-mentioned plants, trees, and/or crops. This post-stress damage can include hail damage, wind damaged, flooding, etc. As long as the plant, tree, and/or crop is alive, the more the damage, the greater the response due to the microbial inoculant composition. Results of the response can be seen in as little as two weeks. If the microbial inoculant composition is applied prior to the damage, the regeneration of the plant, tree, and/or crop can occur immediately or in close proximity in time to the damage.

Figure 6:
FIG. 6. Sunflower subjected to mower damage, then treated with an exemplary microbial inoculant composition.

FIG. 6 shows the Hydra effect that results from treating sunflower with a microbial inoculant composition after the sunflower had been mowed. Not only does the sunflower survive the mowing damage, but treatment with the microbial inoculant composition results in increased branching, increased head count, and increased flower surface area compared to a sunflower that is not subjected to mower damage and treatment with the microbial inoculant composition.

Figure 7:
FIG. 7. Cabbage subjected to mower damage, then treated with an exemplary microbial inoculant composition.

FIG. 7 shows the Hydra effect in cabbage that results from treating cabbage with a microbial inoculant composition after the cabbage had been mowed. Not only does the cabbage survive the mowing damage, but treatment with the microbial inoculant composition results in increased head count and increased head size compared to a cabbage that is not subjected to mower damage and treatment with the microbial inoculant composition.

The microbial inoculant composition can be co-fermented. In at least one example, the microbial inoculant composition includes a mixture of at least one aerobic species and at least one anaerobic species. During co-fermentation, the aerobic microbes typically grow more quickly than anaerobic microbes at first. Eventually, fermentation by the aerobes depletes the fermentation broth of oxygen and produces $CO_2$. Depletion of oxygen in the broth promotes growth of the anaerobic microbes, while accumulation of $CO_2$ in the broth slows growth of the aerobic microbes. In this way, a microbial inoculant composition that includes an aerobic species and an anaerobic species can be prepared in a single co-fermentation. In at least one example, the microbial inoculant composition can be aerated to facilitate growth of the *Pseudomonas* spp.

The microbial inoculant composition may be prepared by incubating the microbes in a suitable culture medium at any suitable temperature. A suitable culture medium can include a carbon source (e.g., cane sugar or sucrose), sufficient white vinegar to adjust the pH of the culture medium to no higher than 7.0 (e.g., no higher than 6.8), iron, and a source of potassium (e.g., potassium nitrate).

The microbes may be incubated at a minimum temperature of at least 5° C., such as, for example, at least 10° C., at least 15° C. at least 20° C., at least 25° C., at least 30° C., or at least 40° C. The microbes may be incubated at a maximum temperature of no more than 50° C., such as, for example, no more than 45° C., no more than 45° C., no more than 40° C., no more than 35° C., or no more than 30° C. The microbes may be incubated at a temperature characterized by any range that includes, as endpoints, any combination of a minimum temperature identified above and any maximum temperature identified above that is greater than the minimum temperature. For example, in some embodiments, the microbes may be incubated at a temperature of from 10° C. to 40° C.

The microbial inoculant composition may be prepared by incubating the microbes in a suitable culture medium for a sufficient time to allow growth of both aerobic and anaerobic microbes in the fermentation culture. When a mixture of aerobic microbes and anaerobic microbes are co-fermented, the microbes may be incubated for a minimum of at least 48 hours, such as, for example, at least 72 hours, at least 96 hours, at least 120 hours, at least 144 hours, or at least 168 hours. The microbes may be incubated for a maximum of no more than 240 hours, no more than 216 hours, no more than 192 hours, no more than 168 hours, no more than 144 hours, no more than 120 hours, or no more than 96 hours. The microbes may be incubated for a period characterized by a range having, as endpoints, any combination of a minimum incubation time listed above and any maximum incubation time listed above that is greater than the minimum incubation time.

The microbial inoculant may be applied to seeds, plants, or a field of plants by any suitable method. As described above, the microbial inoculant composition may be formulated with a biocompatible adhesive agent that allows the microbial inoculant composition to be applied to, and adhere to, a seed. Such a formulation can be a folair liquid, seed coating, seed coating hydrogel, etc. The formulation can be mixed into a seeder at planting or can be mixed prior to planting. Alternatively, the microbial inoculant composition may be formulated into with a biocompatible agents that can be applied to seeds and dried. Suitable agents include, for example, dried tapioca, powdered milk, or gum arabic.

Other application methods can involve applying the microbial inoculant composition to one or more tissues of plant, such as, for example, the root, the stem, one or more leaves, or a seed-producing pod. In such cases, the microbial inoculant composition may be applied by any suitable method including, for example, spraying or ampule delivery. The formulation may be sprayed using, for example, a portable spraying unit, hand-held spraying device, irrigation equipment, or aerial spraying. Ampule delivery may be performed manually or using an automated system.

Still other application methods can involve applying the microbial inoculant composition to the soil or seed bed into which seeds will be planted. In these embodiments, the microbial inoculant composition may be applied by spraying or ampule delivery as described immediately above. Alternatively, the microbial inoculant composition may be applied by drip. In some of these embodiments, the microbial inoculant composition can be applied, whether by spray or by drip, while the soil is being seeded.

Still other application methods can include application as a foliar spray, through an irrigation pivot, and as a seed coat. In at least one example, a seed coat media that can hold water can be used to allow the bacteria to live without drying out. In this example, the bacteria can include primarily non-sporulating bacteria that may die when desiccated.

In some cases, a formulation of the microbial inoculant composition can include a predetermined moisture content. The minimum moisture content can be at least 5% such as, for example, at least 6%, at least 7%, at least 8%, at least 9%, at least 10%, at least 15%, at least 20%, at least 25%, at least 30%, or at least 50%.

In some embodiments, a formulation of the microbial inoculant composition can include a sugar (e.g., cane sugar or sucrose) and vinegar (e.g., white vinegar). The sugar can provide a metabolic carbon source. The vinegar can provide an acidic pH and/or an alternative carbon source. As an alternative to, or in addition to, the use of vinegar to regulate pH, the microbial inoculant composition can include *Lactobacillus plantarum*, as described above, to help maintain an acidic pH once the microbial inoculant composition is applied to the plant.

In other embodiments, a formulation of the microbial inoculant composition can include lactic acid media to provide an acidic pH.

In other embodiments, a formulation of the microbial inoculant composition can include glycerol as a dispersion medium.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Method of Production

Aquatic plants were derived from Long Lake, Codington County S. Dak. that were collected (Eurasian Milfoil root and Bullrush Tuber). These aquatic plant tissues were surface sterilized using a 10% bleach solution for 30 seconds. The tissues were then again surface sterilized with a 30% alcohol bath for five seconds then washed with distilled water for 30 seconds to provide material free of epiphytic bacteria and other microbes. This plant material was then macerated and placed in a room temperature seven-gallon incubator with a solution of sucrose, sufficient vinegar to adjust the pH to no more than 6.8, micronutrients (MICROPLEX, Miller Chemical & Fertilizer, LLC, Hanover, Pa.) to get a final iron concentration of 1 ppm, and ¼ teaspoon of potassium nitrate as a nitrogen source. The mixture was allowed to incubate for seven days to allow for sufficient bacteria to grow.

This mixture was then transferred to a plastic tank at room temperature containing between 2500 gallons and 3000 gallons of dechlorinated water in it with 100 pounds of pure cane sugar and two gallons of vinegar, two pounds of nutrient mixture (MICROPLEX, Miller Chemical & Fertilizer, LLC, Hanover, Pa.), and ¼ cup of potassium nitrate. The solution was allowed to incubate to a concentration of bacteria equal to McFarland standard as determined by visual comparison with known standards to a final bacterial concentration of about $3 \times 10^8$ CFU/ml. This took approximately 10 days to reach this concentration. This mixture was then decanted into shipping containers for application to the field.

The mixture is applied at a rate of one pint per acre using conventional spraying equipment with an application pressure of 50 psi or less and sufficient droplet size to allow for even plant coverage. The farmers were instructed to use de-chlorinated water (using, e.g., commercially-available dechlorinators such as sodium thiosulfate or tetra sodium salts to remove chlorine or chloramines from the water), or well water and not to mix it with other tank introduced chemicals or herbicides. The farmers also were instructed not to apply additional hormones to the plant once the microbial inoculant was applied.

Example 2

The microbial inoculant was prepared as described in Example 1. Naphthaleneacetic acid was added to a final concentration of 2 ppm.

Example 3

The microbial inoculant was prepared as described in Example 1. *Bacillus thuringiensis* was added to the inoculant to a final concentration of $1.5\times10^8$ CFU/ml.

Example 4

The microbial inoculant composition was applied to the plants and early removal of the primary fruit of the plants was performed. A secondary fruit, oftentimes in the form of multiple heads per plant where there was only one, or at least more than the primary fruit, was treated as the primary yield.

Example 5

The microbial inoculant composition can be put in the presence of gamma-aminobutyric acid (GABA) at 500 ppm in water solution, which can cause rapid replication in contrast to plants where the microbial inoculant composition was either not applied or applied but not put in the presence of GABA.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A microbial inoculant composition comprising:
an aquatic *Pseudomonas* species pluralis (spp.);
a *Clostridium* spp.; and
*Brevundimonas kwangchunensis, Fictibacillus barbaricus/Bacillus barbaricus*, a *Prosthecobacter* spp., *Sphingobacterium multivorum*, or a *Sphingomonas* spp.

2. The microbial inoculant composition of claim 1, wherein the aquatic *Pseudomonas* spp. comprises *P. moraviensis, P. mandelii, P. umsongensis*, or *P. fluorescens.*

3. The microbial inoculant composition of claim 1, wherein the *Clostridium* spp. comprises *Clostridium saccharobutylicum.*

4. The microbial inoculant composition of claim 1, further comprising a *Bacillus* spp.

5. The microbial inoculant composition of claim 4, wherein the *Bacillus* spp. comprises *B. megaterium, B. subtilis*, or *B. licheniformis.*

6. The microbial inoculant composition of claim 1, further comprising an aquatic *Delftia* spp.

7. The composition of claim 1, further comprising an aquatic *Chryseobacterium* spp.

8. The microbial inoculant composition of claim 1, further comprising an aquatic *Pseudomonas fluorescens.*

9. The microbial inoculant composition of claim 1, further comprising *Bacillus megaterium, Bacillus amyloliquifaciens, Bacillus subtilus, Bacillus pumilus, Sphingosinicella microcystinivorans, Pseudomonas chlororaphis, Pseudomonas mandelii, Pseudomonas umsongensis*, a *Clostridium* spp., *Arthrobacter ramosus, Streptomyces yogyakartensis*, an *Arthrobacter* spp., a *Xanthomonas* spp., or *Chryseobacterium indologenes.*

10. The microbial inoculant composition of claim 1 further comprising a yeast strain.

11. A method comprising applying the microbial inoculant composition of claim 1 to a tissue of a plant.

12. A method comprising applying the microbial inoculant composition of claim 1 to a surface of a seed.

13. A method comprising applying the microbial inoculant composition of claim 1 to a seed bed.

14. A method comprising applying the microbial inoculant composition of claim 1 to a field comprising a plurality of plants.

* * * * *